United States Patent
Nishikawa et al.

(10) Patent No.: US 7,906,557 B2
(45) Date of Patent: Mar. 15, 2011

(54) ORAL PREVENTIVE/THERAPEUTIC AGENT FOR SKIN DAMAGE CONTAINING DIACYLGLYCERYL ETHER

(75) Inventors: Masazumi Nishikawa, Ibaraki (JP); Itsuki Murota, Ibaraki (JP); Tadakazu Tamai, Ibaraki (JP); Kazuyoshi Yoshikai, Ibaraki (JP)

(73) Assignee: Maruha Nichiro Seafoods, Inc., Tokyo (JP)

( * ) Notice: Subject to any disclaimer, the term of this patent is extended or adjusted under 35 U.S.C. 154(b) by 0 days.

(21) Appl. No.: 10/517,323

(22) PCT Filed: Jun. 17, 2003

(86) PCT No.: PCT/JP03/07662
§ 371 (c)(1),
(2), (4) Date: Dec. 20, 2004

(87) PCT Pub. No.: WO04/000301
PCT Pub. Date: Dec. 31, 2003

(65) Prior Publication Data
US 2005/0220844 A1 Oct. 6, 2005

(30) Foreign Application Priority Data
Jun. 19, 2002 (JP) .................. 2002-178670

(51) Int. Cl.
*A61K 31/08* (2006.01)
(52) U.S. Cl. ........................ 514/715; 514/724
(58) Field of Classification Search .................. 424/401
See application file for complete search history.

(56) References Cited

U.S. PATENT DOCUMENTS

| | | | |
|---|---|---|---|
| 4,046,914 A | 9/1977 | Hallgren et al. | |
| 5,079,003 A | 1/1992 | Scaffidi | |
| 5,514,591 A * | 5/1996 | Levin | 436/62 |
| 5,518,730 A * | 5/1996 | Fuisz | 424/426 |
| 5,602,183 A * | 2/1997 | Martin et al. | 514/724 |
| 5,849,309 A * | 12/1998 | Tanaka et al. | 424/401 |
| 5,942,246 A * | 8/1999 | Mayhew et al. | 424/450 |
| 6,667,053 B1 * | 12/2003 | Ahmad et al. | 424/450 |

FOREIGN PATENT DOCUMENTS

| | | | |
|---|---|---|---|
| EP | 0321428 | * | 12/1988 |
| EP | 0 321 428 A2 | | 6/1989 |
| EP | 0321428 A2 | * | 6/1989 |
| JP | 2-11516 | | 1/1990 |
| JP | 7-82162 | | 3/1995 |
| WO | WO 99/58136 | | 11/1999 |

OTHER PUBLICATIONS

Shark Liver Oil Product Information Sheet.*
Ecomer product information sheet.*
Yanishlieva, N., "Autoxidation of alkoxylipids. II. Alkyldiacylglycerols and dialkylacylglycerole", Chem.Phys.Lipids., vol. 18, No. 2, pp. 149-153, 1977.

* cited by examiner

*Primary Examiner* — Robert A Wax
*Assistant Examiner* — Melissa S Mercier
(74) *Attorney, Agent, or Firm* — Oblon, Spivak, McClelland, Maier & Neustadt, L.L.P.

(57) ABSTRACT

The present invention provides an oral preventive or therapeutic agent for skin damage, containing diacylglyceryl ether as an active ingredient represented by the formula (I):

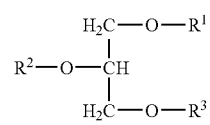

wherein $R^1$ denotes $C_{12-24}$ aliphatic hydrocarbon group having a degree of unsaturation of between 0 and 2; $R^2$ denotes $C_{12-24}$ acyl group having a degree of unsaturation of between 0 and 6; and $R^3$ denotes $C_{12-24}$ acyl group having a degree of unsaturation of between 0 and 6.

18 Claims, No Drawings

ORAL PREVENTIVE/THERAPEUTIC AGENT FOR SKIN DAMAGE CONTAINING DIACYLGLYCERYL ETHER

TECHNICAL FIELD

The present invention relates to an agent for preventing or treating skin damage and particularly relates to an oral preventive or therapeutic agent for skin damage containing diacylglyceryl ether as an active ingredient.

BACKGROUND ART

Appropriate irradiation with sunlight provides beneficial effects for organisms, such as vitamin D synthesis and microbicidal action. However, excessive UV irradiation is extremely hazardous to skin.

For example, ultraviolet B (UVB) radiation with wavelengths ranging from 290 nm to 320 nm reaches the dermic layer of skin so as to damage the DNA of the subcutaneous tissue. Thus, long-time exposure to UVB causes alteration in collagen fibers, formation of wrinkled skin and sagging skin, and also causes pigmentation, such as pigmented spots and freckles. Moreover, skin cancer may be formed.

Furthermore, ultraviolet A (UVA) radiation with wavelengths ranging from 320 nm to 400 nm does not have any direct damaging action. However, UVA is thought to excite photosensitive substances so as to indirectly cause skin melanism (suntan) and the like.

In particular, advancing destruction of the ozone layer due to air pollution caused by, for example, Freon gas has led to recent drastic increases in the quantity of ultraviolet rays reaching the surface of the earth. Hence, protection against ultraviolet rays is an important issue.

To protect skin from ultraviolet rays, many external cosmetics and sunscreen agents have been conventionally developed. A sunscreen agent mainly comprises: an ultraviolet absorber that absorbs ultraviolet rays before they reach the inside of the skin so as to reduce ultraviolet rays reaching the inside of the skin and to protect skin and an agent for scattering ultraviolet rays that causes reflection or scattering of ultraviolet rays to which skin is exposed so as to reduce the quantity of ultraviolet rays reaching the inside of the skin. As an ultraviolet absorber, for example, benzophenone-based 2-hydroxy-4-methoxybenzophenone, p-aminobenzoic acid-based agents, methoxycinnamic acid-based p-methoxycinnamic acid-2-ethylhexyl, salicylic acid-based phenyl salicylate, or 4-tert-butyl-4'-methoxybenzoylmethane is used. Furthermore, as an agent for scattering ultraviolet rays, for example, titanium oxide or zinc oxide is used.

However, it has been indicated that the long-term use of these chemical substances or metals may have adverse effects on skin by, for example, stimulating skin.

Accordingly, a safe and secure means and/or method for protecting skin from damage due to ultraviolet rays have been desired.

DISCLOSURE OF THE INVENTION

In view of the above problems, an object of the present invention is to provide a safe and secure means and/or method for protecting skin from damage due to ultraviolet rays.

As a result of intensive studies, the present inventors have discovered that skin damage such as formation of wrinkled skin and/or sagging skin due to ultraviolet rays, formation of skin cancer, or formation of pigmented spots and/or freckles due to ultraviolet rays can be safely prevented or treated by oral dosage of diacylglyceryl ether, thereby completing the present invention.

Diacylglyceryl ether is broadly distributed in the oils and fats of aquatic animals and is particularly richly contained in oils and fats derived from the liver of sharks or cuttlefish. The physiological action of diacylglyceryl ether has been studied since the 1960s. For example, Brohult, A. reported that the intake of diacylglyceryl ether derived from Greenland sharks is effective against leukopenia or thrombocytopenia that occurs in connection with radiotherapy for cancer patients (Acta Radiol., Suppl. No. 233 (1963)). Most of the mechanism of this effect remains unknown; however, ether linkages (hydrocarbon chains) within the structure of diacylglyceryl ether may be deeply involved in the mechanism.

However, studies about the prevention or treatment of skin damage due to ultraviolet rays through the oral use of diacylglyceryl ether have not been reported to date.

The present invention that solves the above problems provides an oral preventive or therapeutic agent for skin damage, containing diacylglyceryl ether as an active ingredient represented by the formula (I):

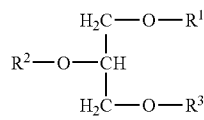

wherein $R^1$ denotes $C_{12-24}$ aliphatic hydrocarbon group having a degree of unsaturation of between 0 and 2; $R^2$ denotes $C_{12-24}$ acyl group having a degree of unsaturation of between 0 and 6; and $R^3$ denotes $C_{12-24}$ acyl group having a degree of unsaturation of between 0 and 6.

The present invention relates to an oral preventive or therapeutic agent for skin damage, containing diacylglyceryl ether as an active ingredient represented by the formula (I):

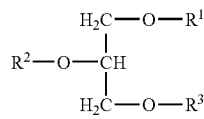

wherein $R^1$ denotes $C_{12-24}$ aliphatic hydrocarbon group having a degree of unsaturation of between 0 and 2; $R^2$ denotes $C_{12-24}$ acyl group having a degree of unsaturation of between 0 and 6; and $R^3$ denotes $C_{12-24}$ acyl group having a degree of unsaturation of between 0 and 6.

Examples of aliphatic hydrocarbon group denoted by $R^1$ include those having a ratio of carbon number to degree of unsaturation represented by 24:1, 22:1, 20:1, 18:2, 18:1, 18:0, 16:1, 16:0, 14:0, or 12:0. A particularly preferred example of aliphatic hydrocarbon group has a ratio of carbon number to degree of unsaturation of 18:1, 18:0, 16:1, or 16:0.

Examples of acyl group denoted by $R^2$ include those having a ratio of carbon number to degree of unsaturation of 24:1 (those derived from nervonic acid), 22:6 (those derived from docosahexaenoic acid), 22:1 (those derived from erucic acid), 20:5 (those derived from eicosapentaenoic acid), 20:4 (those derived from arachidonic acid), 20:1 (those derived from gadoleic acid), 18:3 (those derived from α-linolenic acid or γ-linolenic acid), 18:2 (those derived from linoleic acid), 18:1 (those derived from oleic acid or octadecenoic acid), 18:0 (those derived from stearic acid), 16:1 (those derived from palmitoleic acid), 16:0 (those derived from palmitic acid), 14:0 (those derived from myristic acid), and 12:0 (those derived from lauric acid).

Examples of particularly preferred acyl group denoted by $R^2$ include those having a ratio of carbon number to degree of unsaturation of 24:1 (those derived from nervonic acid), 22:6 (those derived from docosahexaenoic acid), 22:1 (those derived from erucic acid), 20:5 (those derived from eicosapentaenoic acid), 20:1 (those derived from gadoleic acid), 18:1 (those derived from oleic acid or octadecenoic acid), and 16:0 (those derived from palmitic acid).

Examples of acyl group denoted by $R^3$ include those having a ratio of carbon number to degree of unsaturation of 24:1 (those derived from nervonic acid), 22:6 (those derived from docosahexaenoic acid), 22:1 (those derived from erucic acid), 20:5 (those derived from eicosapentaenoic acid), 20:4 (those derived from arachidonic acid), 20:1 (those derived from gadoleic acid), 18:3 (those derived from α-linolenic acid or γ-linolenic acid), 18:2 (those derived from linoleic acid), 18:1 (those derived from oleic acid or octadecenoic acid), 18:0 (those derived from stearic acid), 16:1 (those derived from palmitoleic acid), 16:0 (those derived from palmitic acid), 14:0 (those derived from myristic acid), and 12:0 (those derived from lauric acid).

Particularly preferred examples of acyl group denoted by $R^3$ include those having a ratio of carbon number to degree of unsaturation of 24:1 (those derived from nervonic acid), 22:6 (those derived from docosahexaenoic acid), 22:1 (those derived from erucic acid), 20:5 (those derived from eicosapentaenoic acid), 20:1 (those derived from gadoleic acid), 18:1 (those derived from oleic acid or octadecenoic acid), and 16:0 (those derived from palmitic acid).

The dosage form of the oral preventive or therapeutic agent for skin damage of the present invention is not specifically limited and is appropriately selected and used as necessary. Generally the agent is formulated in the form of oral agents such as tablets, sustained-release tablets, granules, fine-grained agents, chewable tablets, sublingual tablets, and gum.

The oral preventive or therapeutic agent for skin damage of the present invention is formulated in accordance with a conventional technique using an excipient such as starch, lactose, saccharose, mannite, carboxymethylcellulose, corn starch, or inorganic salts.

In addition to the above excipient, binders, disintegrating agents, surfactants, lubricants, agents for promoting flowability, pH regulators, absorption retarders, antioxidants, antiseptics, corrigents, colorants, odorants, or the like can be appropriately used.

Here, specific examples of binders include crystalline cellulose, crystalline cellulose. carmellose sodium, methylcellulose, hydroxypropylcellulose, hydroxypropylcellulose with a low substitution degree, hydroxypropylmethylcellulose 2208, hydroxypropyl methyl cellulose 2906, hydroxypropylmethylcellulose 2910, hydroxypropylmethylcellulosephthalate 200731, hydroxypropylmethylcellulosephthalate 220824, hydroxypropylmethylcellulose acetate succinate, carmellose sodium, ethylcellulose, carboxymethylethylcellulose, hydroxyethylcellulose, wheat starch, rice starch, corn starch, potato starch, dextrin, pregelatinized starch, partially-pregelatinized starch, hydroxypropyl starch, pullulan, polyvinylpyrrolidone K25, polyvinylpyrrolidone K30, aminoalkylmethacrylate copolymer E, aminoalkylmethacrylate copolymer RS, methacrylic acid copolymer L, methacrylic acid copolymer S, methacrylic acid copolymer LD, polyvinylacetaldiethylamino acetate, polyvinyl alcohol, gum Arabic, gum Arabic powder, agar, gelatine, white shellac, gum tragacanth, purified saccharose, macrogol 200, macrogol 300, and macrogol 6000.

Specific examples of disintegrating agents include crystalline cellulose, methylcellulose, hydroxypropylcellulose with a low substitution degree, carmellose, carmellose calcium, carmellose sodium, croscarmellose sodium, wheat starch, rice starch, corn starch, potato starch, partially-pregelatinized starch, hydroxypropyl starch, carboxymethyl starch sodium, and gum tragacanth.

Specific examples of surfactants include soybean lecithin, sucrose fatty acid ester, polyoxyl 40 stearate, polyoxyethylene hardened castor oil 100, polyoxyethylene hardened castor oil 40, polyoxyethylene hardened castor oil 50, polyoxyethylene hardened castor oil 60, polyoxyethylene [42] polyoxypropylene [67] glycol, polyoxyethylene [54] polyoxypropylene [39] glycol, polyoxyethylene [105] polyoxypropylene [5] glycol, polyoxyethylene [160] polyoxypropylene [80] glycol, polyoxyethylene [196] polyoxypropylene [67] glycol, sorbitan sesquioleate, sorbitan trioleate, sorbitan monostearate, sorbitan monopalmitate, sorbitan monolaurate, polysorbate 40, polysorbate 60, polysorbate 65, polysorbate 80, glycerin monostearate, sodium lauryl sulfate, and lauromacrogol.

Specific examples of lubricants include wheat starch, rice starch, corn starch, stearic acid, calcium stearate, magnesium stearate, hydrated silicon dioxide, light anhydrous silicic acid, synthetic aluminum silicate, dried aluminum hydroxide gel, talc, magnesium aluminometasilicate, calcium hydrogen phosphate, anhydrous calcium hydrogen phosphate; sucrose fatty acid ester, waxes, hydrogenated vegetable oil, and polyethylene glycol.

Specific examples of agents for promoting flowability include hydrated silicon dioxide, light anhydrous silicic acid, synthetic aluminum silicate, and magnesium silicate.

Furthermore, the oral preventive or therapeutic agent for skin damage of the present invention can be administered in liquid form, such as suspensions, emulsions, syrups, or elixirs. These various dosage forms may-contain flavoring agents and colorants.

Furthermore, the oral preventive or therapeutic agent for skin damage of the present invention can be added to various foods and drinks without any loss of effects. For example, the oral preventive or therapeutic agent for skin damage of the present invention is appropriately formulated as granules, liquids, or the like. The formulated products are contained in foods such as canned foods, ham and/or sausages, boiled fish paste, bread, cookies, rice crackers, gum, chocolate, ice cream, yogurt, beverages, soup, curry, or stew. Thus, the agent of the present invention can be produced as a processed food.

The oral preventive or therapeutic agent for skin damage of the present invention is formulated and administered at a dose that varies depending on the age, body weight, severity of disease, and similar factors regarding a patient subject to administration. In general, the agent is administered so that the intake of diacylglyceryl ether is within a range between 10 and 5000 mg/day, preferably 100 and 2000 mg/day, and more preferably 500 and 2000 mg/day. Administration can be carried out once a day or at several separate instances a day.

This specification includes part or all of the contents as disclosed in the specification of Japanese Patent Application No. 2002-178670, which is a priority document of the present application.

BEST MODE OF CARRYING OUT THE INVENTION

The present invention will be hereafter described in detail by referring to examples. However, the scope of the present invention is not limited by these examples.

Example 1

An experiment was carried out on prevention or treatment of wrinkles and skin cancer formed by ultraviolet (UVB) irradiation on the skin of the dorsal regions of hairless mice using compositions containing diacylglyceryl ether.
(1) Preparation of a Composition Containing Diacylglyceryl Ether Shark liver oil was subjected to degumming and deacidification treatment and vacuum distillation so as to remove hydrocarbon components, and then subjected to decolorization and steam distillation using active clay, thereby preparing a composition containing diacylglyceryl ether (containing 66.4% diacylglyceryl ether, 26.3% triglyceride, and 7.3% squalene). In addition, the compositions of aliphatic hydrocarbon group and acyl group in diacylglyceryl ether were as shown in Table 1 below.

TABLE 1

Composition (%) of aliphatic hydrocarbon group and acyl group in diacylglyceryl ether

| Structure (carbon number:degree of unsaturation) | Composition (%) of $R^1$ | Composition (%) of $R^2$ and $R^3$ |
| --- | --- | --- |
| 14:1 | 1.8 | 1.7 |
| 16:0 | 11.4 | 18.5 |
| 16:1 | 9.5 | 5.8 |
| 18:0 | 7.7 | 3.7 |
| 18:1 | 52.2 | 37.6 |
| 18:2 | 2.2 | 1.8 |
| 18:3 | trace amounts | 0.9 |
| 18:4 | trace amounts | trace amounts |
| 20:0 | 2.2 | trace amounts |
| 20:1 | 7.2 | 5.4 |
| 20:4 | trace amounts | 1.4 |
| 20:5 | trace amounts | 3.0 |
| 22:1 | 2.2 | 6.1 |
| 22:6 | trace amounts | 1.8 |
| 24:1 | 0.2 | 3.0 |
| Other | 3.4 | 9.3 |

(2) Experimental Procedure 16 female 8-week-old HR-1 hairless mice (CHARLES RIVER JAPAN, INC.) were quarantined and acclimatized for 10 days. The mice were then divided into 2 groups: a group fed with feed containing the above diacylglyceryl ether-containing composition mixed therein (diacylglyceryl ether-containing composition represented 0.55% of the total feed weight) and a control group. The test was then started. The test period is continuous 20 weeks. The mice of each group were fed ad libitum with the feed containing diacylglyceryl ether-containing composition mixed therein or the control feed.

20 weeks later, irradiation with ultraviolet rays at a UVB lump wavelength between 290 nm and 320 nm was carried out at a frequency of 3 times per week for 10 weeks using a UV radiator (Nagai Seisakujo). The UV dose was 1MED (minimal erythemal dose, 14 mJ/cm$^2$) during week 1, 2MED during week 2, 3MED during week 3, and 4MED during week 4 and thereafter. Evaluation was carried out by observing the skin of the dorsal regions 10 weeks after the start of the test, and then determining the degree of wrinkle formation by score evaluation. Furthermore, after 4 weeks of irradiation with ultraviolet rays, the number of individuals developing verrucae that are indicators of skin cancer due to ultraviolet rays was counted. The degree of wrinkle formation was evaluated using the following 4 grades in accordance with the standard of Bissett D. L. et al (Photochem. Photobiol. 46, 367-378, 1987).

Score 0: Numerous fine grooves cover the back and both sides and spread in a longitudinal direction (from the head to tail of each body). These grooves are observed or not observed (disappear) depending on the movement of animals.

Score 1: Fine grooves spread along the dorsal median line. Only a few shallow coarse wrinkles run across the back (spread perpendicular to the body axis), and are observed or not observed (disappear) depending on the movement of animals.

Score 2: Fine grooves spread all over the dorsal region. Some wrinkles run across the back (spread perpendicular to the body axis).

Score 3: Fine grooves spread all over the dorsal region. Deep wrinkles independently run across the back (spread perpendicular to the body axis).

(3) Results

In both the group fed with the feed containing the diacylglyceryl ether-containing composition mixed therein and the control group, wrinkle formation was observed on the skin of the dorsal regions. The average score±standard deviation of all cases in the group fed with the feed containing the diacylglyceryl ether-containing composition mixed therein was 2.0±0.9 and the same in the control group was 2.8±0.4.

Furthermore, while the development of verrucae that are indicators of skin cancer was observed in 7 out of 8 mice in the control group, the development of verrucae was observed in 2 out of 8 mice in the group fed with the feed containing the diacylglyceryl ether-containing composition mixed therein.

In addition, no cases of death were observed in the animals by the end of the experiment.

Based on the test results of Example 1, it was inferred that the feed containing the diacylglyceryl ether-containing composition mixed therein suppressed significantly ($p<0.05$) wrinkle formation due to UVB irradiation and thus was useful in prevention of the formation of wrinkled skin and sagging skin or the formation of skin cancer. In addition, it was clear that the feed containing the diacylglyceryl ether-containing composition mixed therein suppressed the onset of cancer.

Example 2

The effect on ultraviolet erythema of guinea pigs was tested using a composition containing diacylglyceryl ether.
(1) Preparation of Composition Containing Diacylglyceryl Ether A composition containing diacylglyceryl ether (containing 66.4% diacylglyceryl ether, 26.3% triglyceride, and 7.3% squalene) was prepared by a method similar to that in Example 1 (the compositions of aliphatic hydrocarbon group and acyl group in diacylglyceryl ether were similar to those in Table 1).

(2) Experimental Procedure 12 male 5-week-old Hartley guinea pigs (CHARLES RIVER JAPAN, INC.) were quarantined and acclimatized for 7 days. The guinea pigs were then divided into 2 groups: a group administered with the above diacylglyceryl ether-containing composition and a control group, and then the test was started. The test period was 2 continuous weeks and the route of administration was oral administration. The dose of the diacylglyceryl ether composition was 1 g/kg per day. On the day of final administration, the hair of the dorsal regions of the animals was removed using depilatory cream. On the next day, UV erythema was caused to develop by UV irradiation. UV irradiation was carried out by placing a rubber plate provided with 3 small holes (circles with diameters of 10 mm each) on the sites from which hair had been removed, and then carrying out UV irradiation from a height of 20 cm for 40 seconds (0.123 J/cm$^2$) using a UV radiator for erythema formation (TK-151, Unicom). 4 hours after irradiation, erythema formation was visually observed and then evaluated with the following 4 grades using the total of the results obtained at the 3 exposed sites.
0: No erythema was formed.
1: Erythema with unclear boundaries was formed on an area half or less that of the entire irradiated area.
2: Erythema with unclear boundaries was formed.
3: Clear erythema was formed.
(3) Results In both the group administered with the diacylglyceryl ether-containing composition and the control group, at 4 hours after UV irradiation, erythema was observed on all irradiated sites in all cases. The average score±standard deviation of all cases in the group administered with the diacylglyceryl ether-containing composition was 6.7±1.9 and that in the control group was 7.7±1.4.

In addition, no cases of death were observed in the animals by the end of the experiment.

Based on the test results of experiment 2, it was inferred that because the diacylglyceryl ether-containing composition showed a tendency to suppress UV erythema formation, the composition is useful in alleviation of skin redness (sunburn) or melanism (suntan).

Example 3

Acute toxicity of a diacylglyceryl ether-containing composition was-tested.
(1) Preparation of Diacylglyceryl Ether-Containing Composition A diacylglyceryl ether-containing composition (containing 66.4% diacylglyceryl ether, 26.3% triglyceride, and 7.3% squalene) was prepared (the compositions of aliphatic hydrocarbon group and acyl group in diacylglyceryl ether were similar to those in Table 1) using a method similar to that in Example 1.
(2) Experimental Procedure Male 6-week-old SD rats (CHARLES RIVER JAPAN, INC.) were quarantined and acclimatized for 7 days. 5 rats were used per group and subjected to an acute toxicity test using the diacylglyceryl ether-containing composition at doses of 5, 10, 20 and 40 g/kg body weight. Administration was carried out by forced oral administration using a sonde tube (single administration). On day 7 after administration, the rats were sacrificed under anesthesia by exsanguination via abdominal aorta and then subjected to autopsy.
(3) Results Regarding the conditions and behavior of the rats, the movement of the rats of all groups became somewhat slower immediately after administration, harsh breath was observed by 4 hours after administration, and loose stool was observed for one day. However, subsequently, abnormalities were not particularly observed in behavior or the like. No cases of death were confirmed among the animals of any of the groups (the median lethal dose (LD50) was 40 g/kg or more). Regarding body weight, although the body weights of the group administered at a dose of 40 g/kg body weight remained unchanged for 3 days after administration, increases in terms of body weight were observed in all the groups. No differences (ANOVA) among the administered groups were observed in body weight changes. In addition, no abnormalities thought to result from the effect of the test substance were observed in organs or the like that were subjected to autopsy after the end of the test.

Example 4

A toxicity test was carried out by repetitive administration of a diacylglyceryl ether-containing composition.
(1) Preparation of Diacylglyceryl Ether-Containing Composition A diacylglyceryl ether-containing composition (containing 66.4% diacylglyceryl ether, 26.3% triglyceride, and 7.3% squalene) was prepared using a method similar to that in Example 1 the compositions of aliphatic hydrocarbon group and acyl group in diacylglyceryl ether were similar to those in Table 1).
(2) Experimental Procedure 9-week-old SD rats (CHARLES RIVER JAPAN, INC.) were quarantined and acclimatized for 7 days. The diacylglyceryl ether-containing composition was administered at doses of 1 and 2 g/kg body weight to 2 male and 2 female rats per group, so that a toxicity test using repetitive administration was carried out for 14 days. Administration was carried out by forced oral administration using a gastric tube. On the day following the end of administration, the rats were sacrificed under anesthesia by exsanguination via abdominal aorta, and then subjected to autopsy.
(3) Results Regarding the conditions and behavior of the rats, the movement of the rats of all groups became slower and harsh breath was observed by approximately 6 hours after administration on the first day. In addition, by the time 3 days after the start of administration, we felt the movement to be somewhat slow, although it was not same slow movement as that observed on the first day. However, subsequently, abnormalities were not particularly observed in terms of feed and water intake during the period, and no cases of diarrhea or the like were observed. As a result of autopsy, abnormalities thought to result from the effect of the administered substance were not observed in organs or the like.

Next, an example of the oral preventive or therapeutic agent for skin damage containing dicylglyceryl ether of the present invention is shown.

Example 5

Through the use of the following raw materials, the oral preventive or therapeutic agent for skin damage of the present invention was formulated as a soft gelatin capsule in accordance with a method conventionally used in the art.

TABLE 2

| | |
|---|---|
| diacylglyceryl ether | 125 mg |
| triglyceride | 100 mg |
| squalene | 23 mg |
| ethyl parahydroxybenzoate | 2 mg |
| Total | 250 mg |

Example 6

Through the use of the following raw materials, boiled fish paste containing the oral preventive or therapeutic agent for skin damage of the present invention was produced in accordance with a method conventionally used in the art.

TABLE 3

| | |
|---|---|
| diacylglyceryl ether | 2 g |
| triglyceride | 1.5 g |
| squalene | 0.1 g |
| emulsifier | 2.5 g |
| minced fish | 100 g |
| common salt | 2.5 g |
| starch | 4.0 g |
| sodium glutamate | 1.0 g |
| sugar | 1.5 g |
| ice water | 45 g |

Example 7

Through the use of the following raw materials, soup containing the oral preventive or therapeutic agent for skin damage of the present invention was produced in accordance with a method conventionally used in the art.

TABLE 4

| | |
|---|---|
| diacylglyceryl ether | 2.5 g |
| triglyceride | 2 g |
| squalene | 0.5 g |
| sweet corn | 250.0 g |
| butter | 30 g |
| onion | 20 g |
| wheat flour | 15 g |
| cow milk | 200 ml |
| common salt | 1.5 g |
| pepper | 0.1 g |
| sugar | 1 g |
| garlic | 5 mg |
| celery | 5 mg |
| laurel | 1 mg |
| sodium glutamate | 0.1 g |
| sodium inosinate | 0.01 g |

Example 8

Through the use of the following raw materials, retort curry containing the oral preventive or therapeutic agent for skin damage of the present invention was produced in accordance with a method conventionally used in the art.

TABLE 5

| | |
|---|---|
| diacylglyceryl ether | 6 g |
| triglyceride | 5 g |
| squalene | 1 g |
| carrot | 100 g |
| potato | 300 g |
| onion | 200 g |
| beef | 300 g |
| curry powder | 5 g |
| wheat flour | 30 g |
| common salt | 5 g |
| pepper | 1 g |
| sugar | 0.1 g |
| sodium glutamate | 1 g |

All publications, patents, and patent applications cited herein are incorporated herein by reference in their entirety.

INDUSTRIAL APPLICABILITY

Through the oral dosage of the oral preventive or therapeutic agent for skin damage containing diacylglyceryl ether according to the present invention, skin damage such as wrinkle formation and/or sagging formation, the formation of skin cancer, or the formation of pigmented spots and/or freckles resulting from ultraviolet rays can be safely prevented or treated.

The invention claimed is:

1. A method of reducing at least one skin damage in a subject in need thereof, comprising orally administering to the subject in need thereof a composition comprising diacylglyceryl ether represented by the formula (I), triglyceride, and squalene; in an amount sufficient to reduce the at least one skin damage:

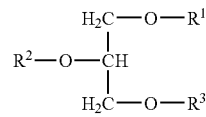

wherein $R^1$ denotes $C_{12-24}$ aliphatic hydrocarbon group having a degree of unsaturation of between 0 and 2; $R^2$ denotes $C_{12-24}$ acyl group having a degree of unsaturation of between 0 and 6; and $R^3$ denotes $C_{12-24}$ acyl group having a degree of unsaturation of between 0 and 6, and wherein the at least one skin damage is selected from the group consisting of formation of skin cancer induced by ultraviolet light, formation of pigmented spots induced by ultraviolet light, formation of freckles induced by ultraviolet light, the formation of wrinkles induced by ultraviolet light, the formation of verrucae induced by ultraviolet light, and the formation of erythema induced by ultraviolet light.

2. The method of claim 1, wherein the diacylglyceryl ether, in the composition, is orally administered at a dosage of between 10 mg and 5000 mg per day.

3. The method of claim 1, wherein the composition is provided in the form of a processed food.

4. The method of claim 1, wherein the diacylglyceryl ether, in the composition, is orally administered at a dosage of between 100 mg and 2000 mg per day.

5. The method of claim 1, wherein the at least one diacylglyceryl ether, in the composition, is orally administered at a dosage of between 500 mg and 2000 mg per day.

6. The method of claim 1, wherein the composition is provided in liquid form.

7. The method of claim 6, wherein the liquid form is a suspension, emulsion, syrup, or elixir.

8. The method of claim 1, wherein the composition is provided in the form of a tablet, sustained-release tablet, granule, fine-grained agent, chewable tablet, sublingual tablet, or gum.

9. The method of claim 1, wherein the oral administering is carried out once a day or at several separate instances a day.

10. The method of claim 1, wherein the composition further comprises at least one further component selected from the group consisting of an excipient, a binder, a disintegrating agent, a surfactant, a lubricant, an agent for promoting flowability, a pH regulator, an absorption retarder, an antioxidant, an antiseptic, a corrigent, a colorant, an odorant, and mixtures thereof.

11. The method of claim 1, wherein the at least one skin damage is the formation of skin cancer induced by ultraviolet light.

12. The method of claim 1, wherein the at least one skin damage is the formation of freckles induced by ultraviolet light.

13. The method of claim 1, wherein the at least one skin damage is the formation of pigmented spots induced by ultraviolet light.

14. The method of claim 1, wherein the at least one skin damage is the formation of verrucae induced by ultraviolet light.

15. The method of claim 1, wherein the at least one skin damage is the formation of erythema induced by ultraviolet light.

16. The method of claim 1, wherein the composition comprises 66.4% diacylglyceryl ether represented by the formula (I), 26.3% triglyceride, and 7.5% squalene.

17. The method of claim 16, wherein the composition is prepared from degummed shark liver oil.

18. The method of claim 1, wherein the composition is prepared from degummed shark liver oil.

* * * * *